US00PP19047P2

(12) United States Plant Patent
Lim

(10) Patent No.: US PP19,047 P2
(45) Date of Patent: Jul. 22, 2008

(54) SHRUB ROSE PLANT NAMED 'BAIRLS'

(50) Latin Name: *Rosa hybrida*
Varietal Denomination: BAIrls

(75) Inventor: Peter P. Lim, McMinnville, OR (US)

(73) Assignee: Bailey Nurseries, Inc., Newport, MN (US)

( * ) Notice: Subject to any disclaimer, the term of this patent is extended or adjusted under 35 U.S.C. 154(b) by 0 days.

(21) Appl. No.: 11/809,233

(22) Filed: May 31, 2007

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent L Bell
(74) *Attorney, Agent, or Firm*—Penny J. Aguirre

(57) ABSTRACT

A new cultivar of shrub rose, *Rosa* 'BAIrls', characterized by its clusters of fragrant, double flowers that are deep pink in color with a white eye, its compact and rounded plant habit and its recurrent blooming habit. The new variety has medium green glossy foliage that is resistant to black spot and powdery mildew, is readily propagated on its own roots and is hardy in U.S.D.A. Zones 5 to 9.

2 Drawing Sheets

Botanical classification: *Rosa hybrida.*
Variety denomination: 'BAIrls'.

BACKGROUND OF THE INVENTION

The present invention relates to a new and distinct cultivar of *Rosa hybrida.* The new cultivar will be referred to hereafter by its cultivar name, 'BAIrls'. 'BAIrls' is a shrub rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of shrub rose, 'BAIrls', designated as seedling No 98H224 was selected among seedlings derived from a cross made in Yamhill, Oreg. in 1998 between the female parent, 'KORimro' (Not patented) and the male parent, 'Flower Carpet' (U.S. Plant Pat. No. 7,282). 'BAIrls' was selected as unique and budded onto understock and reselected by the inventors for its distinct characteristics in 2004.

The new cultivar has been asexually propagated by rooting of softwood cuttings from a plant grown on its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of two years in Yamhill, Oreg. and evaluated at several other test sites in the U.S. These attributes in combination distinguish 'BAIrls' as a unique cultivar of shrub rose.

1. 'BAIrls' exhibits double flowers that are deep pink in color with a white eye. Classified as deep pink by American Rose Society standards.
2. 'BAIrls' exhibits a compact and rounded plant form with a height of 60 to 90 cm.

3. 'BAIrls' exhibits medium green foliage.
4. 'BAIrls' is a recurrent bloomer.
5. 'BAIrls' has shown excellent resistance to rose blackspot (*Diplocarpon rosae*) and powdery mildew (*Sphaerotheca pannosa* var. *rosa*).
6. 'BAIrls' has flowers that exhibit as slight rose fragrance.
7. 'BAIrls' is hardy in U.S.D.A. Zones 5 to 9.
8. 'BAIrls' is a vigorous grower and readily propagated by softwood cuttings and grown on its own roots.

The new cultivar of shrub rose can be readily distinguished from its parents and other cultivars. The female parent, 'KORimko', has flowers that are light pink to near white and has a groundcover habit. The male parent, 'Flower Carpet', has semi-double deep pink flowers with a lighter pink reverse and dark green glossy foliage. The cultivars 'BAIief' (U.S. Plant Pat. No. 17,196) and 'Winnipeg Parks' (U.S. Plant Pat. No. 9,122) are the closest comparison roses. They both have similarity to 'BAIrls' in that they are shrub roses having deep pink flowers. They differ from 'BAIrls' in that 'BAIief' has smaller flowers, an upright arching growth habit and is everblooming while 'Winnipeg Parks' has larger flowers that lack a white eye and is everblooming.

BRIEF DESCRIPTION OF THE DRAWING

The accompanying colored photographs illustrate the overall appearance and distinct characteristics of the new shrub rose, 'BAIrls', as grown outdoors in trial blocks and containers in St. Paul, Minn. and Yamhill, Oreg. The photographs were taken of two year-old plants grown on their own roots.

Figure 1:
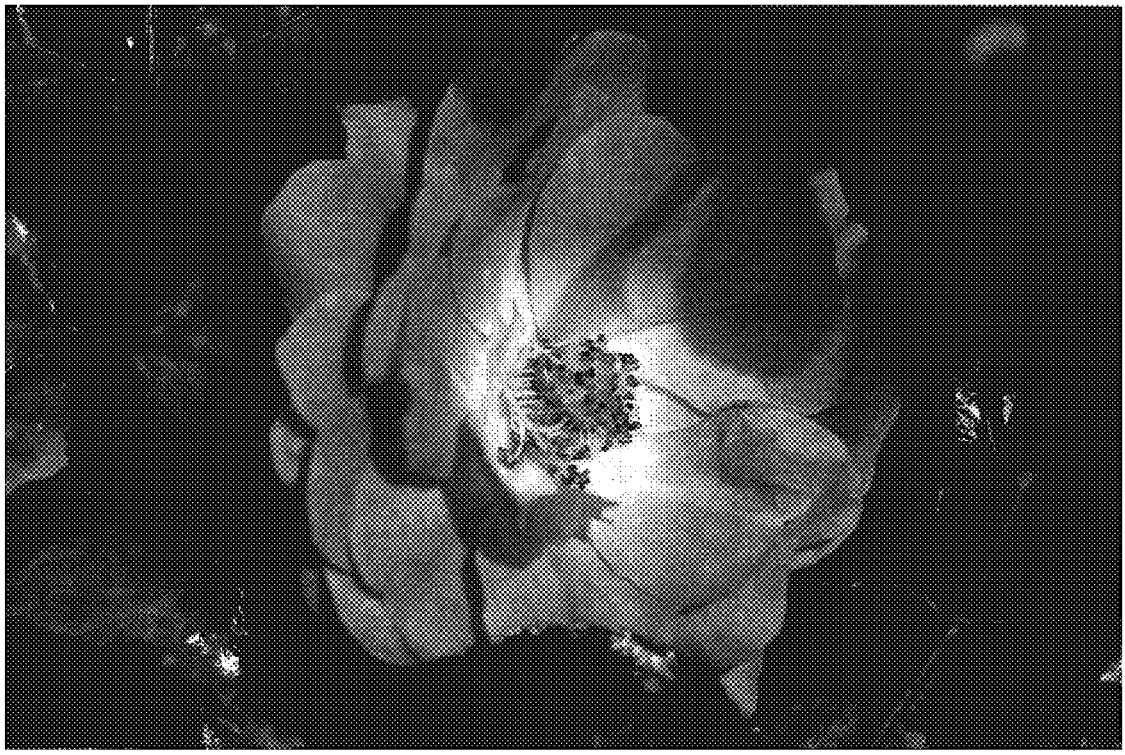
FIG. 1 provides a view of a fully open flower.
Figure 2:
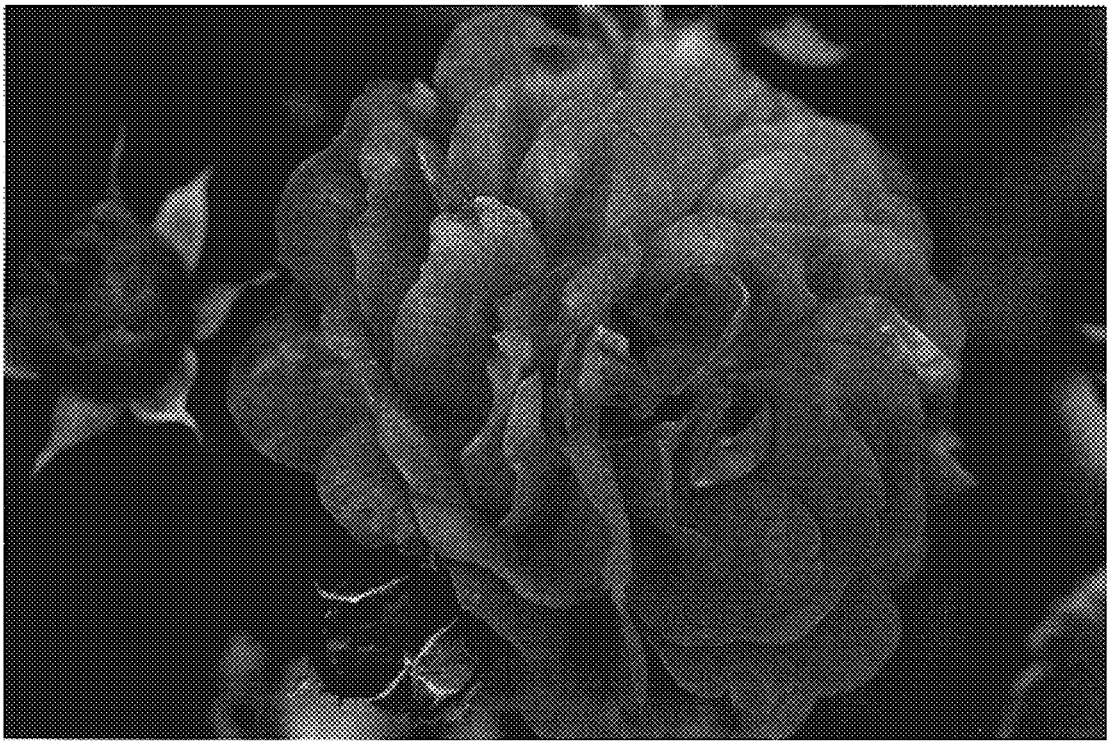
FIG. 2 provides a view of a newly open flower and flower buds just prior to opening.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two year-old container plants and field-grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification.*—*Rosa hybrida* 'BAIrls'.

*Parentage.*—Seed parent *Rosa* 'KORimro', pollen parent *Rosa* 'Flower Carpet'.

*Blooming habit.*—Abundant in May and June and recurrent throughout the growing season.

*Plant habit.*—Compact and rounded.

*Height and spread.*—Reaches 60 to 90 cm in height and 60 cm to 1 M in spread.

*Cold hardiness.*—U.S.D.A. Zone 5 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young and maturing; between 144A to 144B, mature wood; 197A with areas of 197D showing through ridges.

*Stem surface.*—Young and mature; glabrous, adult wood; mostly glabrous with bark-like ridges;

*Stem size.*—Average of 3 mm in width , up to 11 cm in length.

*Thorns.*—Narrowly triangular in shape, slightly curved downward, oval base, average of 4 per 5 cm in number, average of 5 mm in length and with a base 3.5 mm in length and 2 mm in width, 176A to 176B in color.

Foliage description:

*Leaves.*—Division is odd-pinnate, arrangement is alternate, average of 6.5 cm in length and 4 cm in width, internode length is an average of 1.2 cm.

*Leaflets.*—5 to 7, orbicular to ovate in shape, rounded base, acute to obtuse apex, serrated (appear crenate like) margins, glabrous and glossy on upper surface and finely pubescent on lower surface, average of 2.2 cm in length and 1.5 cm in width (lateral leaves), color: young leaves upper surface; color between 137A and 144A, young leaves lower surface: 137C mature leaves upper surface; 137A, mature leaves lower surface; 138A, pinnately veined (not conspicuous).

*Rachis.*—Average of 3.5 cm in length and 1.2 mm in diameter, color of upper surface 137B with center ridge 144D, color of lower surface 137B, surface is glabrous with small prickles on margin and underside and thorns on underside (about 3 per rachis).

*Stipules.*—Parallel with auricle facing outward, adnate to petiole, average of 8 mm in length and 3 mm in width, color on upper side is 137B with 144D on middle ridge, color of lower surface is 137B, surface is glabrous on upper surface with prickles on lower surface.

*Petioles.*—Average of 1.5 cm in length and 1.2 mm in diameter, 137B with center 144D, color of lower surface 137B, glabrous with prickles on margin and lower surface.

Inflorescence description:

*Inflorescence type.*—Typically corymbs of 3 to 4 flowers of double, rosette formed flowers.

*Flower number.*—Average of 1 per lateral stem, about 10 per 2 gallon plant.

*Flower fragrance.*—Light rose scent.

*Flower longevity.*—About 3 to 5 days, depending on temperature and sunlight exposure.

*Flower type.*—Double.

*Flower size.*—Average of 4 cm in diameter and 2 cm in depth.

*Peduncles.*—Stiff, average of 2 cm in length and 2 mm in diameter, glabrous, color is 144C becoming suffused with 178A with maturity, prickled surface.

*Bracts.*—Average of 2 to 3 per flower, average of 1.7 cm in length and 3 mm in width, lanceolate in shape, ciliate margins, acuminate to leaf-like apex, and truncate base, sessile, glabrous, color of upper surface 137A near apex and 144C near center, color of lower surface 137A with 144C in center near base.

*Flower buds.*—Ovate in shape, medium in size with an average of 1.8 cm in length and 1 cm in width prior to opening, color 53C.

*Sepals.*—5, broadly lanceolate in shape, margin is entire with sporadic foliaceous appendages, color of upper surface is 138A, color of lower surface is a blend of 138A and 144A, upper surface is tomentose, lower surface is pubescent and covered with short dark prickles, average of 1.8 cm in length and 6 mm in width, apex is apiculate to changing to leaf-like, base is truncate, aspect is upright in tight bud stage changing to horizontal when flower opens.

*Petals.*—About 20, drop readily and cleanly, broadly obovate in shape and curled under on sides and margins, upper and lower surface is glabrous and satiny, entire margin, cuneate base, apex is rounded to emarginate, average of 1.8 cm in length and 1.5 cm in width (inner petals smaller), color: opening flowers upper and lower surface: N57B blended towards base with N57C and veins N57A, fully open flowers upper and lower surface; blend of 62A through 62D, fading flowers upper and lower surface; 62D suffused with some 62C, base petal spot; 155B.

*Receptacle.*—Average of 5 mm in diameter and 6 mm in depth when flower is fully open, urn shaped, glabrous and satiny, color is 144A.

*Pistils.*—About 10, stigma is an average of 0.5 mm in length and width and 165A in color, style is an average of 5 mm in length and 138D in color, average of 8 petaloid pistils, same color as petals and about 6 mm in length and 2.5 mm in width.

*Stamens.*—About 60, filaments are about 5 mm in length and 162D in color, anthers are an average of 1 mm in length, an average of 0.5 mm in width and 165A in color, pollen is moderate in quantity and 163A in color.

*Hips.*—Round and red-orange in color.

I claim:

1. A new and distinct cultivar of shrub rose plant named 'BAIrls' as herein illustrated and described.

* * * * *